(12) United States Patent
Pham et al.

(10) Patent No.: US 6,558,419 B1
(45) Date of Patent: May 6, 2003

(54) INTRAOCULAR LENS

(75) Inventors: Hai-Minh Pham, Huntington Beach, CA (US); Tuan Anh Nguyen, Orange, CA (US)

(73) Assignee: Bausch & Lomb Incorporated, Rochester, NY (US)

(*) Notice: Subject to any disclaimer, the term of this patent is extended or adjusted under 35 U.S.C. 154(b) by 0 days.

(21) Appl. No.: 10/005,864

(22) Filed: Nov. 8, 2001

(51) Int. Cl.$^7$ .................................................. A61F 2/16
(52) U.S. Cl. ....................... 623/6.16; 623/4.1; 623/6.11; 623/6.38; 623/6.25; 623/6.43
(58) Field of Search ............................. 623/4, 5, 6, 4.1, 623/6.11, 6.16, 6.25, 6.38, 6.43

(56) References Cited

U.S. PATENT DOCUMENTS

| | | | |
|---|---|---|---|
| 4,738,680 A | 4/1988 | Herman | 623/6 |
| 5,002,569 A | 3/1991 | Lindstrom | 623/6 |
| 5,171,320 A | 12/1992 | Nishi | 623/6 |
| 5,445,636 A | 8/1995 | Bretton | 606/41 |
| 5,445,637 A | 8/1995 | Bretton | 606/41 |
| 5,620,013 A | 4/1997 | Bretton | 128/898 |
| 5,693,093 A | 12/1997 | Woffinden | 623/6 |
| 5,885,279 A | 3/1999 | Bretton | 606/41 |
| 6,015,435 A * | 1/2000 | Valunin et al. | 623/6.28 |
| 6,089,234 A | 7/2000 | Bretton | 128/898 |
| 6,106,554 A | 8/2000 | Bretton | 623/6.62 |
| 6,138,680 A | 10/2000 | Bretton | 128/898 |
| 6,162,249 A | 12/2000 | Deacon | 623/6.16 |
| 6,264,692 B1 | 7/2001 | Woffinden | 623/6.17 |

OTHER PUBLICATIONS

Vargas, et al., *Posterior Capsule Opacification (PCO) in Three Modern Single Piece Foldable Intraocular Lenses (IOLs): A Clinicopathological Study*, Center for Research on Ocular Therapeutic and Biodevices, Storm Eye Institute, Dept. of Ophthalmology, Medical University of South Carolina, Charleston, South Carolina, 3/01.

Nishi, et al., "Inhibition of Migrating Lens Epithelial Cells at the Capsular Bend Created by the Rectangular Optic Edge of a Posterior Chamber Intraocular Lens," *Ophthalmic Surgery and Lasers*, vol. 29, No. 7, pp. 587–594, 7/98.

Nishi, et al., "Preventing Posterior Capsule Opacification by Creating a Discontinuous Sharp Bend in the Capsule," *J. Cataract Refract. Surg.*, vol. 25, pp. 521–526, 4/99.

Nishi, et al., "The Inhibition of Lens Epithelial Cell Migration by a Discontinuous Capsular Bend Created by a Band-Shaped Circular Loop or a Capsule–Bending Ring," *Ophthalmic Surgery and Lasers*, vol. 29, No. 2, pp. 119–125, 2/98.

Nishi, et al., "Explantation of Endocapsular Posterior Chamber Lens After Spontaneous Posterior Dislocation,", vol. 22, pp. 272–275, 3/96.

Mullner–Eidenbock et al., "Cellular Reaction on the Anterior Surface of 4 Types of Intraocular Lenses," *J. Cataract Refract. Surg.*, vol. 27, pp. 734–740, 5/01.

Majima, et al., "Shape of Lens Epithelial Cells After Intraocular Lens Implanation," *J. Cataract Refract. Surg.*, vol. 27, 745–752, 5/01.

Nishi, et al., "Capsule–Bending Ring for the Prevention of Capsular Opacification: A Prelminary Report," *Ophthalmic Surgery and Lasers*, vol. 29, No. 9., pp. 749–753, 9/98.

Nishi, "Posterior Capsule Opacification Part I: Experimental Investigations," *J. Cataract Refract. Surg.*, vol. 25, pp. 106–115, 1/99.

(List continued on next page.)

Primary Examiner—David J. Isabella
Assistant Examiner—Kamrin Landrem
(74) Attorney, Agent, or Firm—Katherine McGuire

(57) ABSTRACT

An intraocular lens for inhibiting posterior capsular opacification, or secondary cataract, includes an optic having a periphery provided with at least two sharp edges which lie radially spaced from each other with respect to the optical axis of the lens optic.

7 Claims, 3 Drawing Sheets

OTHER PUBLICATIONS

Oshika, et al., "Adhesion of Lens Capsule to Intraocular Lenses of Polymethylmethacrylate, Silicone, and Acrylic Foldable Materials: An Experimental Study," *Br J Opthalmol.*, pp. 549–553, 1998.

Hollick, et al., "The Effect of Polymethylmethacrylate, Silicone, and Polyacrylic Intraocular Lenses on Posterior Capsular Opacification 3 Years after Cataract Surgery," *Ophthalmology*, vol. 106, No. 1, pp. 49–55, 1–99.

* cited by examiner

INTRAOCULAR LENS

BACKGROUND OF THE INVENTION

The present invention relates to intraocular lenses (IOLs) for implantation in an aphakic eye where the natural lens has been removed due to damage or disease (e.g., a cataractous lens). The present invention more particularly relates to a novel IOL designed to inhibit the unwanted growth of lens epithelial cells (LECs) between the IOL and posterior capsular bag, also known as posterior capsule opacification or "PCO" to those skilled in the art.

A common and desirable method of treating a cataract eye is to remove the clouded, natural lens and replace it with an artificial IOL in a surgical procedure known as cataract extraction. In the extracapsular extraction method, the natural lens is removed from the capsular bag while leaving the posterior part of the capsular bag (and preferably at least part of the anterior part of the capsular bag) in place within the eye. In this instance, the capsular bag remains anchored to the eye's ciliary body through the zonular fibers. In an alternate procedure known as intracapsular extraction, both the lens and capsular bag are removed in their entirety by severing the zonular fibers and replaced with an IOL which must be anchored within the eye absent the capsular bag. The intracapsular extraction method is considered less attractive as compared to the extracapsular extraction method since in the extracapsular method, the capsular bag remains attached to the eye's ciliary body and thus provides a natural centering and locating means for the IOL within the eye. The capsular bag also continues its function of providing a natural barrier between the aqueous humor at the front of the eye and the vitreous humor at the rear of the eye.

One known problem with extracapsular cataract extraction is posterior capsule opacification, or secondary cataract, where proliferation and migration of lens epithelial cells occur along the posterior capsule behind the IOL posterior surface which creates an opacification of the capsule along the optical axis. This requires subsequent surgery, such as an Er:YAG laser capsulotomy, to open the posterior capsule and thereby clear the optical axis. Undesirable complications may follow the capsulotomy. For example, since the posterior capsule provides a natural barrier between the back of the eye vitreous humor and front of the eye aqueous humor, removal of the posterior capsule allows the vitreous humor to migrate into the aqueous humor which can result in serious, sight-threatening complications. It is therefore highly desirable to prevent posterior capsule opacification in the first place and thereby obviate the need for a subsequent posterior capsulotomy.

Various methods have been proposed in the art to prevent or at least minimize PCO and thus also the number of Er:YAG laser capsultomies required as a result of PCO. These PCO prevention methods include two main categories: mechanical means and pharmaceutical means.

In the mechanical means category of PCO prevention, efforts have been directed at creating a sharp, discontinuous bend in the posterior capsule wall which is widely recognized by those skilled in the art as an effective method for minimizing PCO. See, for example, *Posterior Capsule Opacification* by Nishi, *Journal of Cataract & Refractive Surgery*, Vol. 25, January 1999. This discontinuous bend in the posterior capsule wall can be created using an IOL having a posterior edge which forms a sharp edge with the peripheral wall of the IOL.

In the pharmaceutical means of PCO prevention, it has been proposed to eliminate LEC and/or inhibit LEC mitosis by using an LEC-targeted pharmaceutical agent. See, for example, U.S. Pat. No. 5,620,013 to Bretton entitled "Method For Destroying Residual Lens Epithelial Cells". While this approach is logical in theory, putting such a method into clinical practice is difficult due to complications arising, for example, from the toxicity of some of the LEC inhibiting agents themselves (e.g., saporin), as well as the difficulty in ensuring a total kill of all LECs in the capsular bag. Any remaining LECs may eventually multiply and migrate over the IOL, eventually resulting in PCO despite the attempt at LEC removal at the time of surgery.

By far the most promising method for inhibiting LEC formation on the posterior surface of an IOL is the mechanical means, i.e., by designing the IOL to have a sharp peripheral edge particularly at the posterior surface—peripheral edge juncture to create a discontinuous bend in the posterior capsule wall. This discontinuous bend in the posterior capsule wall has been clinically proven to inhibit the growth and migration of LECs past this bend and along the IOL surface. One of the early reports of this PCO-inhibiting effect of a planoconvex IOL may be found in *Explanation of Endocapsule Posterior Chamber Lens After Spontaneous Posterior Dislocation* by Nishi et al, J Cataract & Refractive Surgery-Vol 22, March 1996 at page 273 wherein the authors examined an explanated planoconvex PMMA IOL where the posterior surface of the IOL was planar and formed a square edge with the peripheral edge of the IOL:

> "Macroscopic view of the explanted IOL and capsule revealed a 9.5 mm capsule diameter. The open circular loops fit well along the capsule equator. The capsule equator not in contact with the haptic was also well maintained (FIG. 3). An opaque lens mass (Soemmering's ring cataract) was seen between the haptics and optic. The posterior capsule facing the IOL optic was clear.
>
> Histopathological examination of the explanted capsule revealed few epithelial cells (LECs) on the posterior capsule. Between the loops and the optic, a lens mass with accumulation at the edge of the optic was seen (FIG. 4). There was an obvious bend in the posterior capsule at this site." (Emphasis added.)

Thus, in the years since this report, the industry has seen much activity on creating IOLs with sharp posterior edges so as to create a sharp, discontinuous bend in the posterior capsule wall. While IOLs having a sharp posterior edge have proven to inhibit PCO compared to IOLs having rounded edges at the posterior surface-peripheral edge juncture, there still remains the possibility of LECs migrating along the posterior capsule and behind the IOL surface, especially if there is uneven contact and force of the IOL periphery with the capsular bag. This may happen, for example, should the IOL move within the capsular bag following surgery. There therefore remains a need for an improved IOL design which addresses the problem of LEC migration and subsequent PCO formation despite having an IOL with a single sharp posterior edge.

SUMMARY OF THE INVENTION

The present invention addresses the problem of PCO formation beyond the first sharp posterior edge of an IOL by providing an IOL having a periphery including at least two, radially spaced, sharp edges defined by the posterior edge and peripheral walls which extend substantially parallel to the optical axis of the IOL and an interceding peripheral wall which extends substantially perpendicular to the optical axis. This configuration of the periphery of the IOL optic is a significant improvement over the single square edge optic designs in that it provides improved barriers against LEC migration. The optic periphery design is also relatively easy to manufacture compared with other, more complicated IOL periphery designs which have been proposed in the prior art for inhibiting LEC migration. See, for example, the following patents and publications which show various IOL optic periphery designs:

U.S. Pat. No. 5,171,320 issued to Nishi on Dec. 15, 1992

U.S. Pat. No. 5,693,093 issued to Woffinden et al on Dec. 2, 1997

U.S. Pat. No. 6,162,249 issued to Deacon et al on Dec. 19, 2000

BRIEF DESCRIPTION OF THE DRAWING

FIG. 4b is a cross-sectional view of the inventive IOL as taken generally along the line 4b—4b of FIG. 4a;

DETAILED DESCRIPTION

Figure 1:
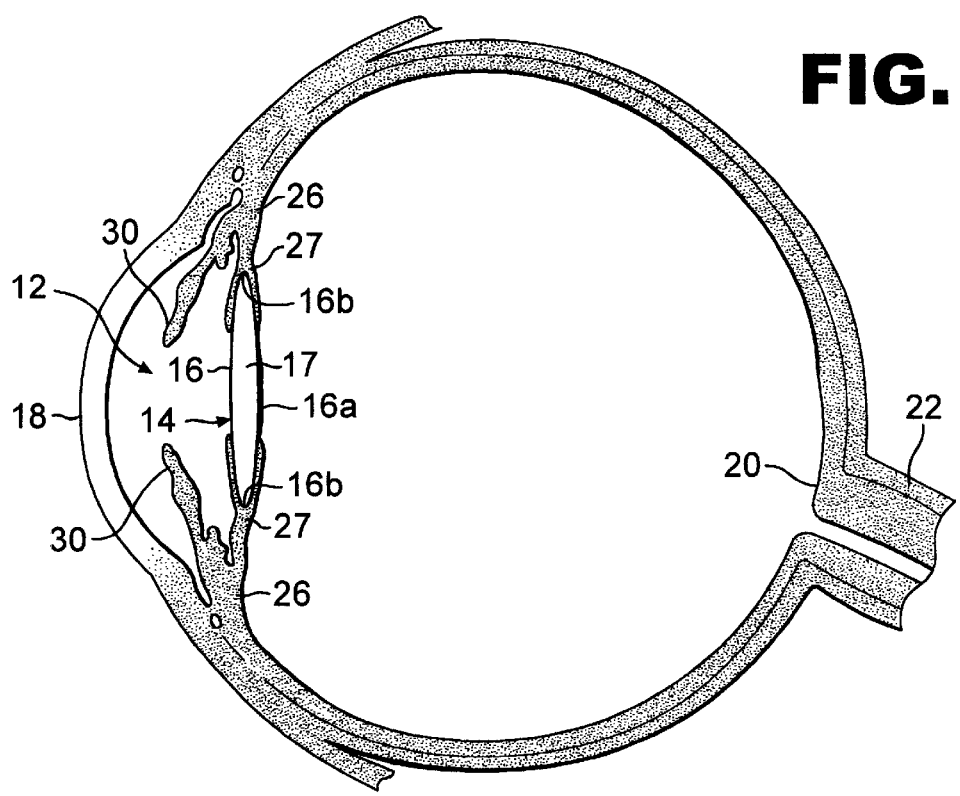
FIG. 1 is a cross-sectional view of a human eye showing the natural lens within the capsular bag of the eye.

Referring now to the drawing, there is seen in FIG. 1 a cross-sectional view of a human eye 10 having an anterior chamber 12 and a posterior chamber 14 separated by the iris 30. Within the posterior chamber 14 is a capsule 16 which holds the eye's natural crystalline lens 17. Light enters the eye by passing through the cornea 18 to the crystalline lens 17 which act together to direct and focus the light upon the retina 20 located at the back of the eye. The retina connects to the optic nerve 22 which transmits the image received by the retina to the brain for interpretation of the image.

In an eye where the natural crystalline lens has been damaged (e.g., clouded by cataracts), the natural lens is no longer able to properly focus and direct incoming light to the retina and images become blurred. A well known surgical technique to remedy this situation involves removal of the damaged crystalline lens which may be replaced with an artificial lens known as an intraocular lens or IOL such as prior art IOL 24 seen in FIGS. 2 and 3. Although there are many different IOL designs as well as many different options as to exact placement of an IOL within an eye, the present invention concerns itself with an IOL for implanting inside the substantially ovoid-shaped capsule 16 of eye 10. This implantation technique is commonly referred to in the art as the "in-the-bag" technique. In this surgical technique, a part of the anterior portion of the capsular bag is cut away (termed a "capsularhexis") while leaving the posterior capsule 16a intact and still secured to the ciliary body 26.

Thus, in the "in-the-bag" technique of IOL surgery, the IOL is placed inside the capsule 16 which is located behind the iris 30 in the posterior chamber 14 of the eye. An IOL includes a central optic portion 24a which simulates the extracted natural lens by directing and focusing light upon the retina, and further includes a means for securing the optic in proper position within the capsular bag. A common IOL structure for securing the optic is called a haptic which is a resilient structure extending radially outwardly from the periphery of the optic. In a particularly common IOL design, two haptics 24b, 24c extend from opposite sides of the optic and curve to provide a biasing force against the inside of the capsule which secures the optic in the proper position within the capsule (see FIG. 2).

Figure 2:
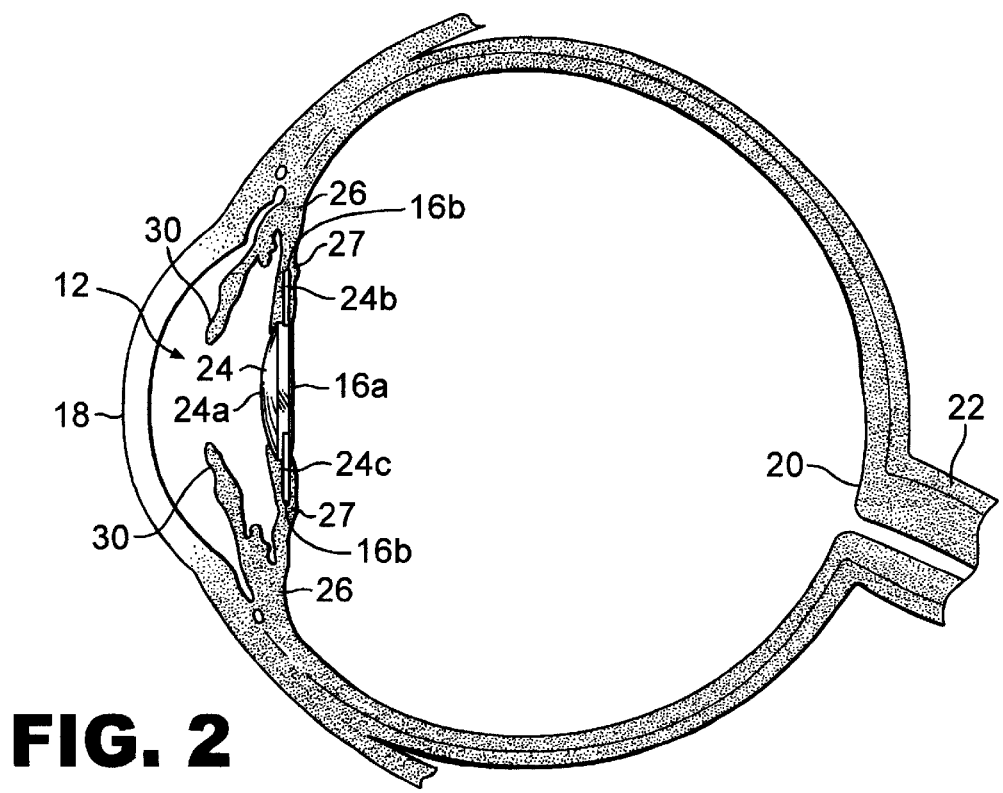
FIG. 2 is a cross-sectional view of a human eye showing the natural lens removed and replaced with a prior art IOL.
Figure 3:
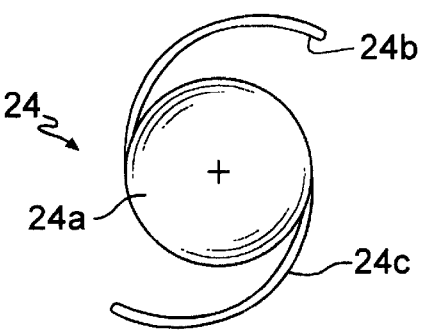
FIG. 3 is a plan view of a prior art IOL.

As stated in the Background section hereof, an undesirable post-surgical condition known as posterior capsule opacification or PCO may occur which results in an implanted IOL becoming clouded and thus no longer able to properly direct and focus light therethrough. The main cause for this condition is the mitosis and migration of lens epithelial cells (LECs) across the posterior surface of the capsule behind the IOL optic. As seen in FIG. 2, the posterior surface 16a of the capsule 16 touches the posterior surface of the IOL optic 24a. When the damaged natural lens is surgically removed, a number of LECs may remain within the capsule 16, particularly at the equator 16b thereof which is the principle source of germinal LECs. Although a surgeon may attempt to remove all LECs from the capsular bag at the time of IOL implantation surgery, it is nearly impossible to remove every single LEC. Any remaining LECs can multiply and migrate along the posterior capsule wall 16a. This is especially true in IOLs having rounded edges, where it has been found that clinically significant PCO results in about 20%–50% of patients three years post surgery. A presently popular and effective method of preventing PCO is to create a sharp, discontinuous bend in the posterior capsule wall 16a as explained in the Background section hereof.

Figure 4A:
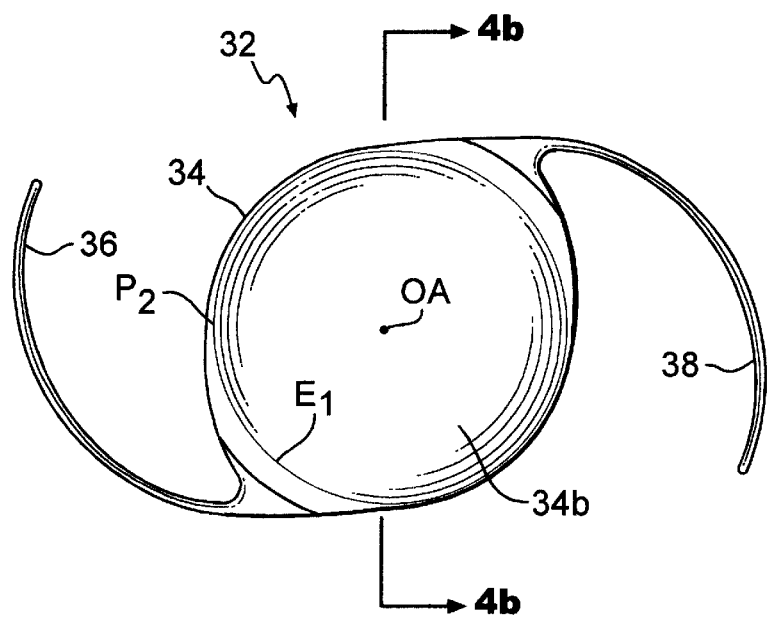
FIG. 4a is a plan view of an IOL made in accordance with the present invention.
Figure 4B:
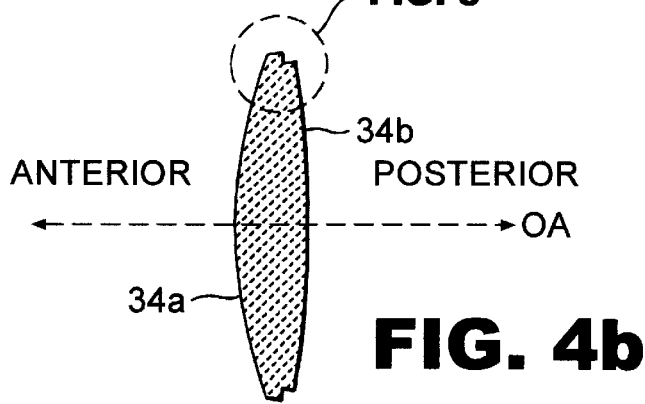

Referring now to FIGS. 4a,b and 5, a first embodiment of the inventive IOL 32 is shown. IOL 32 is seen to include a central optic portion 34 having opposite anterior and posterior surfaces 34a and 34b, respectively. When implanted within the eye, anterior optic surface 34a faces the cornea 18 and posterior optic surface 34b faces the retina 20. A pair of haptics 36,38 are attached to and extend from opposite sides of the periphery of optic portion 34 and are configured to provide a biasing force against the interior of the capsule 16 to properly position IOL 32 therein. More particularly, the haptics 36,38 are configured such that upon implanting the IOL with the capsular bag, the haptics engage the interior surface of the capsular bag. The engagement between the haptics and capsule creates a biasing force causing the IOL optic 34 to vault posteriorly toward the retina 20 whereupon the posterior surface 34b of the IOL optic presses tightly against the interior of the posterior capsule wall 16a of capsule 16. It is noted that other known IOL positioning means are possible and within the scope of the invention. Furthermore, IOL 32 may be made from any suitable IOL material, e.g., PMMA, silicone, hydrogels and composites thereof The IOL 32 may also be a one piece or multiple piece design (e.g. where the haptics are attached to the optic after the optic is formed.) Referring still to FIGS. 4a,b and 5, it is seen that IOL optic 34 has a periphery including a first sharp edge E1 defined at the juncture of posterior surface 34b and peripheral wall P1. With the haptics 36,38 providing the biasing force explained above, the optic posterior surface 34b presses tightly against the posterior capsule wall 16a. Since capsule 16 is somewhat resilient in nature, the force of the IOL optic against the capsule wall results in the IOL indenting into the posterior capsule wall. The first sharp edge E1 of the IOL optic thus forcibly indents into the capsule wall and thereby creates a discontinuous bend in the posterior capsule wall at this point as indicated at arrow B1 in FIGS. 5 and 6. As explained above, this discontinuous bend B1 in the posterior capsule wall 16a acts to inhibit LEC migration past this point (i.e., between the posterior capsule wall 16a and IOL posterior surface 34b) and PCO is inhibited.

Figure 5:
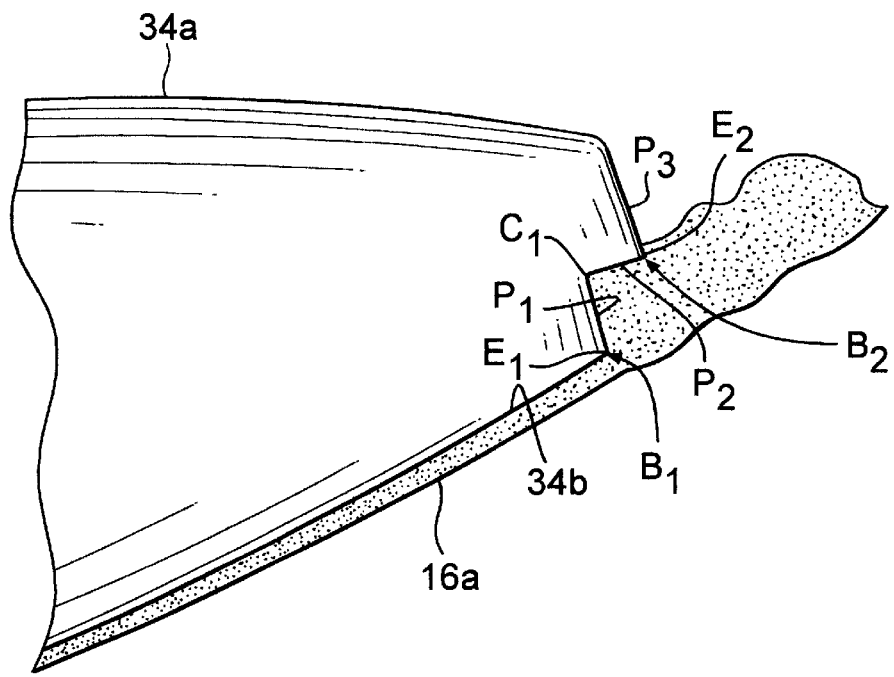
FIG. 5 is an enlarged, fragmented, cross-sectional view showing the detail of the peripheral wall configuration of the IOL of the present invention.

Referring still to FIG. 5, it is seen that the periphery of IOL optic 34 further includes an inner right angle corner C1 defined at the juncture of first peripheral wall P1 and second peripheral wall P2 which are oriented substantially perpendicular to each other. A second sharp edge E2 is defined at the juncture of peripheral walls P2 and P3 which also lie substantially perpendicular to each other. The provision of at least two sharp edges E1 and E2 in the periphery of the IOL optic provides multiple barriers against migrating LECs.

It is noted that the degree to which the IOL indents into the posterior capsule may vary among patients. In some patients, the IOL may indent such that only first sharp edge E1 is engaging the posterior capsule in which case a single discontinuous bend B1 would be provided in the capsule wall to inhibit LEC migration. In this situation, second sharp edge E2 still provides a discontinuous geometry which acts to discourage LECs which may have attached to the IOL from migrating toward and onto the anterior surface 34a of the IOL optic. In other patients, the IOL may indent further into the posterior capsule in which case both first sharp edge E1 and second sharp edge E2 are engaging the posterior capsule (FIG. 5), thereby creating first and second bends B1 and B2 therein, respectively. Thus, in either case, LEC migration is inhibited.

As mentioned above, the primary source of germinating LECs is at the equator 16b of the capsular bag which is located radially outwardly of the optic periphery (FIG. 2). As LECs multiply, they begin migrating radially inwardly along the capsular bag. In a patient where the optic indents into the posterior capsule as seen in FIG. 5, once the LECs reach the IOL optic 34, they will encounter second sharp bend B2 in the capsule formed by IOL sharp edge E2. This sharp bend B2 provides the first barrier against migrating LECs. However, should any LECs continue to migrate inwardly past the bend B2, they will then encounter first sharp bend B1 in the capsule. The provision of more than one sharp bend in the capsule provides more than one barrier against migrating LECs. The present invention thus provides a peripheral edge configuration substantially preventing the chance of LEC migration along the posterior capsule.

It is furthermore noted that the multiple sharp edge configuration of the inventive IOL provides a more complex frill formation in the capsule than the single sharp edge IOL designs of the prior art. In this regard, see the Nishi article cited herein (JCRS January 1995) which explains how it is the complex frill formation at the capsular bend which is believed to inhibit LEC migration.

A presently preferred method of forming the multiple sharp edge configuration in the IOL optic 34 comprises a milling operation where the IOL optic is mounted to a fixture and a mill is used to cut into the posterior optic surface at the perimeter thereof The depth of the mill cut, as measured from the edge of posterior surface 34b to surface wall P2, is preferably about 0.01–1.5 mm, more preferably about 0.05–1.0 mm, and most preferably is about 0.08 mm. The width of the mill cut, as measured from wall P1 to wall P3, is preferably at least about 0.03 mm. Other methods which may be employed to form the peripheral edge geometry include lathing and molding, for example. It is also preferred that IOL 32 undergo tumble polishing prior to forming the edge geometry so as to ensure the edges E1, E2, E3, etc., retain their sharpness.

Figure 6:
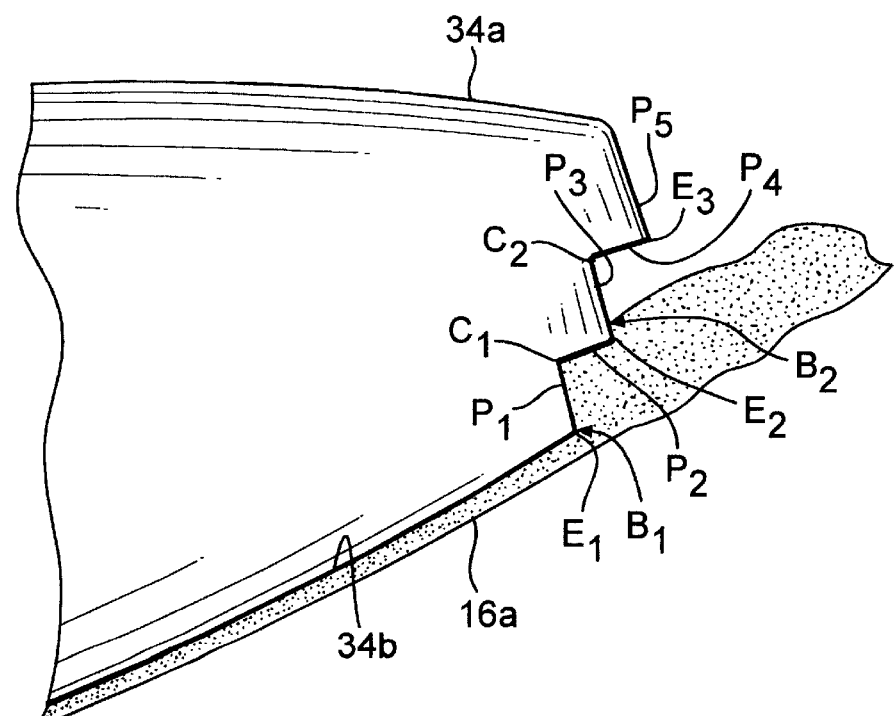
FIG. 6 is the view of FIG. 5 showing an alternate embodiment of the peripheral wall configuration of the IOL of the present invention.

FIG. 6 shows an alternate embodiment of the inventive IOL which further includes a third sharp edge E3 which is defined at the juncture of perpendicular wall surfaces P4 and P5. FIG. 6 illustrates third sharp edge E3 as not engaging capsule 16, however, it is possible that in some patients the optic periphery will indent even deeper into the capsule wall whereupon sharp edge E3 would engage the capsule wall. If the third sharp edge E3 does in fact engage the capsule wall, a third bend in the capsule wall (not shown) would form, providing yet another barrier against LEC migration as explained with respect to sharp edges E1 and E2 above. In the case where third sharp edge E3 does not engage the capsule, it still provides a discontinuous geometry which acts to discourage LECs which may have attached to the IOL from migrating toward and onto the anterior surface 34a of the IOL optic. It will thus be appreciated that the unique multiple sharp edge geometry of the present invention provides multiple barriers against LEC migration both posteriorly and anteriorly of the optic regardless of how deeply the optic indents into the posterior capsule.

It is thus seen that the sharp edges are formed in a radially spaced configuration which gives a "stepped" configuration to the IOL optic periphery. It will be appreciated that any number of sharp edges may be provided in the stepped edge configuration described herein. Moreover, the peripheral wall surfaces P1, P3, P5 extend along spaced, parallel planes which extend substantially parallel to the optical axis OA of the IOL optic (see FIGS. 4a,b), while the interceding peripheral wall surfaces P2 and P4 extend along planes which are substantially perpendicular to the optical axis OA. This unique peripheral configuration provides an IOL which substantially inhibits PCO as described above.

What is claimed is:

1. An intraocular lens for implanting in a human eye, comprising:
    a) a lens optic having opposite anterior and posterior surfaces defined by an optic periphery and further having an optical axis extending through said lens optic; and
    b) at least two sequential sharp edges formed in said optic periphery wherein, with respect to said optical axis, said second sharp edge is located radially outwardly of said first sharp edge, and said first sharp edge is defined by said optic posterior surface and a first peripheral wall lying substantially parallel to said optical axis.

2. The lens of claim 1, and further comprising means for positioning said intraocular lens within a human eye.

3. The lens of claim 2 wherein said positioning means comprises one or more haptics extending from said optic periphery.

4. The intraocular lens of claim 3, wherein said haptics apply a biasing force against said optic in the direction of said posterior optic surface upon implanting said intraocular lens in said human eye.

5. The lens of claim 1, wherein said second sharp edge is defined by second and third peripheral walls with said second peripheral wall lying substantially perpendicular to said optical axis and said third peripheral wall lying substantially parallel to said optical axis.

6. The intraocular lens of claim 5, wherein a third sharp edge is formed in said optic periphery radially outwardly of said second sharp edge.

7. The intraocular lens of claim 6, wherein said third sharp edge is defined by fourth and fifth peripheral walls with said fourth peripheral wall lying substantially perpendicular to said optical axis and said fifth peripheral wall lying substantially parallel to said optical axis.

* * * * *